United States Patent
Timken

(10) Patent No.: US 11,473,016 B2
(45) Date of Patent: *Oct. 18, 2022

(54) CIRCULAR ECONOMY FOR PLASTIC WASTE TO POLYETHYLENE AND LUBRICATING OIL VIA CRUDE AND ISOMERIZATION DEWAXING UNITS

(71) Applicant: Chevron U.S.A. Inc., San Ramon, CA (US)

(72) Inventor: Hye-Kyung Timken, Albany, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 112 days.

This patent is subject to a terminal disclaimer.

(21) Appl. No.: 17/131,850

(22) Filed: Dec. 23, 2020

(65) Prior Publication Data

US 2021/0189252 A1    Jun. 24, 2021

Related U.S. Application Data

(60) Provisional application No. 62/952,669, filed on Dec. 23, 2019.

(51) Int. Cl.
*C10G 1/10* (2006.01)
*C07C 4/04* (2006.01)
(Continued)

(52) U.S. Cl.
CPC ............. *C10G 1/10* (2013.01); *C07C 4/04* (2013.01); *C08F 10/02* (2013.01); *C10B 53/07* (2013.01);
(Continued)

(58) Field of Classification Search
CPC .......... C10G 1/10; C10G 1/002; C10G 45/58; C10G 2300/1003; C10G 2400/02;
(Continued)

(56) References Cited

U.S. PATENT DOCUMENTS

| | | |
|---|---|---|
| 3,845,157 A | 10/1974 | Woo et al. |
| 4,108,730 A | 8/1978 | Chen et al. |

(Continued)

FOREIGN PATENT DOCUMENTS

EP    0620264 A2    10/1994

OTHER PUBLICATIONS

International Search Report and Written Opinion dated Mar. 17, 2021 in PCT/US2020/066799.

*Primary Examiner* — Ellen M McAvoy

(74) *Attorney, Agent, or Firm* — E. Joseph Gess; Melissa M. Hayworth; Terrence M. Flaherty

(57) ABSTRACT

Provided is a continuous process for converting waste plastic into recycle for polyethylene polymerization. In one embodiment, the process comprises selecting waste plastics containing polyethylene and/or polypropylene and passing the waste plastics through a pyrolysis reactor to thermally crack at least a portion of the polyolefin waste and produce a pyrolyzed effluent. The pyrolyzed effluent is separated into offgas, a naphtha/diesel fraction, a heavy fraction, and char. The naphtha/diesel fraction is passed to a crude unit distillation column in a refinery where a straight run naphtha ($C_5$-$C_8$) fraction or a propane/butane ($C_3$-$C_4$) fraction is recovered. The straight run naphtha fraction ($C_5$-$C_8$) or the propane/butane ($C_3$-$C_4$) fraction is passed to a steam cracker for ethylene production. The heavy fraction from the pyrolysis unit can also be passed to an isomerization dewaxing unit to produce a base oil.

25 Claims, 3 Drawing Sheets

(51) Int. Cl.
*C10G 45/58* (2006.01)
*C08F 10/02* (2006.01)
*C10M 177/00* (2006.01)
*C10M 105/04* (2006.01)
*C10B 53/07* (2006.01)
*C10G 1/00* (2006.01)
*C10N 70/00* (2006.01)

(52) U.S. Cl.
CPC ............. *C10G 1/002* (2013.01); *C10G 45/58* (2013.01); *C10M 105/04* (2013.01); *C10M 177/00* (2013.01); *C10G 2300/1003* (2013.01); *C10G 2300/202* (2013.01); *C10G 2300/205* (2013.01); *C10G 2300/305* (2013.01); *C10G 2300/308* (2013.01); *C10G 2300/4006* (2013.01); *C10G 2300/4012* (2013.01); *C10G 2300/4018* (2013.01); *C10G 2400/02* (2013.01); *C10G 2400/04* (2013.01); *C10G 2400/08* (2013.01); *C10G 2400/10* (2013.01); *C10M 2203/024* (2013.01); *C10M 2290/026* (2013.01); *C10M 2290/04* (2013.01); *C10N 2070/00* (2013.01)

(58) Field of Classification Search
CPC ....... C10G 2400/04; C07C 4/04; C08F 10/02; C10B 53/07; C10M 105/04; C10M 177/00; C10N 2070/00
See application file for complete search history.

(56) References Cited

U.S. PATENT DOCUMENTS

| | | | |
|---|---|---|---|
| 4,642,401 A | 2/1987 | Coenen et al. | |
| 5,849,964 A | 12/1998 | Holighaus et al. | |
| 5,981,818 A | 11/1999 | Purvis | |
| 6,143,940 A | 11/2000 | Miller et al. | |
| 6,150,577 A | 11/2000 | Miller et al. | |
| 6,288,296 B1 | 9/2001 | Miller et al. | |
| 6,774,272 B2 | 8/2004 | Miller | |
| 6,822,126 B2 | 11/2004 | Miller | |
| 7,531,703 B2* | 5/2009 | Ramesh | C08J 11/16 201/23 |
| 7,834,226 B2 | 11/2010 | Miller | |
| 8,088,961 B2 | 1/2012 | Miller | |
| 8,404,912 B1 | 3/2013 | Miller | |
| 8,420,875 B1* | 4/2013 | Mackay | C10G 1/02 241/23 |
| 8,480,880 B2 | 7/2013 | Miller | |
| 8,696,994 B2 | 4/2014 | Miller | |
| 10,233,395 B2 | 3/2019 | Ward et al. | |
| 10,260,011 B2 | 4/2019 | Ward et al. | |
| 11,174,436 B2* | 11/2021 | Timken | C10B 53/07 |
| 11,174,437 B2* | 11/2021 | Timken | C10G 51/023 |
| 2002/0179493 A1 | 12/2002 | Etter | |
| 2007/0179326 A1 | 8/2007 | Baker | |
| 2007/0238912 A1 | 10/2007 | Smith | |
| 2014/0121426 A1* | 5/2014 | Tandon | C10G 1/10 422/187 |
| 2015/0080624 A1* | 3/2015 | Gephart | C10G 19/00 422/200 |
| 2015/0247096 A1 | 9/2015 | Barger et al. | |
| 2016/0045841 A1 | 2/2016 | Kaplan et al. | |
| 2016/0177186 A1* | 6/2016 | Tandon | C10B 47/30 202/117 |
| 2016/0264885 A1 | 9/2016 | Narayanaswamy et al. | |
| 2016/0362609 A1 | 12/2016 | Ward et al. | |
| 2018/0355256 A1* | 12/2018 | Dooley | C10G 1/002 |
| 2019/0144755 A1* | 5/2019 | Atkins | C10B 27/06 201/15 |
| 2019/0161683 A1 | 5/2019 | Narayanaswamy et al. | |
| 2019/0177652 A1* | 6/2019 | Atkins | C10G 47/16 |
| 2020/0199325 A1* | 6/2020 | Yao | C07C 51/487 |
| 2021/0130699 A1 | 5/2021 | Bitting | |
| 2021/0189248 A1 | 6/2021 | Timken | |
| 2021/0189250 A1 | 6/2021 | Timken | |
| 2021/0189251 A1 | 6/2021 | Timken | |
| 2021/0189253 A1 | 6/2021 | Timken | |
| 2021/0189254 A1 | 6/2021 | Timken | |
| 2021/0189269 A1 | 6/2021 | Timken | |
| 2021/0388271 A1* | 12/2021 | Randazzo | C10B 49/14 |

* cited by examiner

Establishment of Circular Economy for Recycle of PE via Pyrolysis of PE/PP Waste Plastics Through Oil Refinery Operation Plastic Type Classification for Waste Plastics Recycling

CIRCULAR ECONOMY FOR PLASTIC WASTE TO POLYETHYLENE AND LUBRICATING OIL VIA CRUDE AND ISOMERIZATION DEWAXING UNITS

CROSS REFERENCE TO RELATED APPLICATIONS

The present application claims priority to U.S. Provisional Application No. 62/952,669 filed Dec. 23, 2019, the complete disclosure of which is incorporated herein by reference in its entirety.

BACKGROUND

The world has seen extremely rapid growth of plastics production. According to PlasticsEurope Market Research Group, the world plastics production was 335 million tons in 2016, 348 million tons in 2017 and 359 million tons in 2018. According to McKinsey & Company, the global plastics-waste volume was estimated about 260 million tons per year in 2016, and projected to be 460 million tons per year by 2030 if the current trajectory continues.

Single use plastic waste has become an increasingly important environmental issue. At the moment, there appear to be few options for recycling polyethylene and polypropylene waste plastics to value-added chemical and fuel products. Currently, only a small amount of polyethylene and polypropylene is recycled via chemical recycling, where recycled and cleaned polymer pellets are pyrolyzed in a pyrolysis unit to make fuels (naphtha, diesel), stream cracker feed or slack wax.

Processes are known which convert waste plastic into hydrocarbon lubricants. For example, U.S. Pat. No. 3,845,157 discloses cracking of waste or virgin polyolefins to form gaseous products such as ethylene/olefin copolymers which are further processed to produce synthetic hydrocarbon lubricants. U.S. Pat. No. 4,642,401 discloses the production of liquid hydrocarbons by heating pulverized polyolefin waste at temperatures of 150-500° C. and pressures of 20-300 bars. U.S. Pat. No. 5,849,964 discloses a process in which waste plastic materials are depolymerized into a volatile phase and a liquid phase. The volatile phase is separated into a gaseous phase and a condensate. The liquid phase, the condensate and the gaseous phase are refined into liquid fuel components using standard refining techniques. U.S. Pat. No. 6,143,940 discloses a procedure for converting waste plastics into heavy wax compositions. U.S. Pat. No. 6,150,577 discloses a process of converting waste plastics into lubricating oils. EP0620264 discloses a process for producing lubricating oils from waste or virgin polyolefins by thermally cracking the waste in a fluidized bed to form a waxy product, optionally using a hydrotreatment, then catalytically isomerizing and fractionating to recover a lubricating oil.

Other documents which relate to processes for converting waste plastic into lubricating oils include U.S. Pat. Nos. 6,288,296; 6,774,272; 6,822,126; 7,834,226; 8,088,961; 8,404,912 and 8,696,994; and U.S. Patent Publication Nos. 2019/0161683; 2016/0362609; and 2016/0264885. The foregoing patent documents are incorporated herein by reference in their entirety.

The current method of chemical recycling via pyrolysis cannot make a big impact for the plastics industry. The current pyrolysis operation produces poor quality fuel components (naphtha and diesel range products), but the quantity is small enough that these products can be blended into fuel supplies. However, this simple blending cannot continue if very large volumes of waste polyethylene and polypropylene are to be recycled to address environmental issues. The products as produced from a pyrolysis unit are of too poor quality to be blended in large amounts (for example 5-20 vol. % blending) in transportation fuels.

In order to achieve recycling of single use plastics in an industrially significant quantity to reduce its environmental impact, more robust processes are needed. The improved processes should establish "circular economy" for the waste polyethylene and polypropylene plastics where the spent waste plastics are recycled effectively back as starting materials for polymers and high value byproducts.

SUMMARY

Provided is a continuous process for converting waste plastic into recycle for polyethylene polymerization. The process comprises selecting waste plastics containing polyethylene and/or polypropylene and passing the waste plastics through a pyrolysis reactor to thermally crack at least a portion of the polyolefin waste and produce a pyrolyzed effluent. The pyrolyzed effluent is separated into offgas, a naphtha/diesel fraction, a heavy fraction, and char.

The incorporation of the process with an oil refinery is an important aspect of the present process, and allows the creation of a circular economy with a single use waste plastic such as polyethylene. Thus, the naphtha/diesel fraction is passed to a crude unit in a refinery. A straight run naphtha ($C_5$-$C_8$) fraction is recovered from the crude unit distillation column and passed to a steam cracker for ethylene production. The heavy fraction from the pyrolysis unit can be passed to an isomerization dewaxing unit to produce a base oil.

In another embodiment, a continuous process for converting waste plastic comprising polyethylene into recycle for polyethylene polymerization is provided. The process comprises selecting waste plastics containing polyethylene and polypropylene and passing the waste plastics through a pyrolysis reactor to thermally crack at least a portion of the polyolefin waste and produce a pyrolyzed effluent. The pyrolyzed effluent is separated into offgas, a naphtha/diesel fraction, a heavy fraction, and char. The naphtha/diesel fraction is passed to a crude unit in a refinery from which is recovered a propane and butane ($C_3$-$C_4$) fraction. The ($C_3$-$C_4$) fraction is passed to a steam cracker for ethylene production. The heavy fraction from the pyrolysis unit can be passed to an isomerization dewaxing unit to produce a lubricating base oil.

The refinery will generally have its own hydrocarbon feed flowing through the refinery units. The flow volume of naphtha/diesel or a waxy heavy fraction generated from the pyrolysis of waste plastic to the refinery units can comprise any practical or accommodating volume % of the total flow to the refinery units. Generally, the flow of fractions generated from the waste plastic pyrolysis, for practical reasons, can be up to about 50 vol. % of the total flow, i.e., the refinery flow and the fraction flow. In one embodiment, the flow of the naphtha/diesel is an amount up to about 20 vol. % of the total flow.

Among other factors, it has been found that by adding refinery operations one can upgrade the waste pyrolysis oil and wax to higher value products such as gasoline, jet, diesel, and base oil. Also, by adding refinery operations it has been found that clean naphtha ($C_5$-$C_8$) or $C_3$-$C_4$ can be efficiently and effectively produced from the waste pyrolysis oil for ultimate polyethylene polymer production. Positive economics are realized for the overall process from recycled plastics to a polyethylene product with product quality identical to that of virgin polymer.

DETAILED DESCRIPTION

Figure 1:
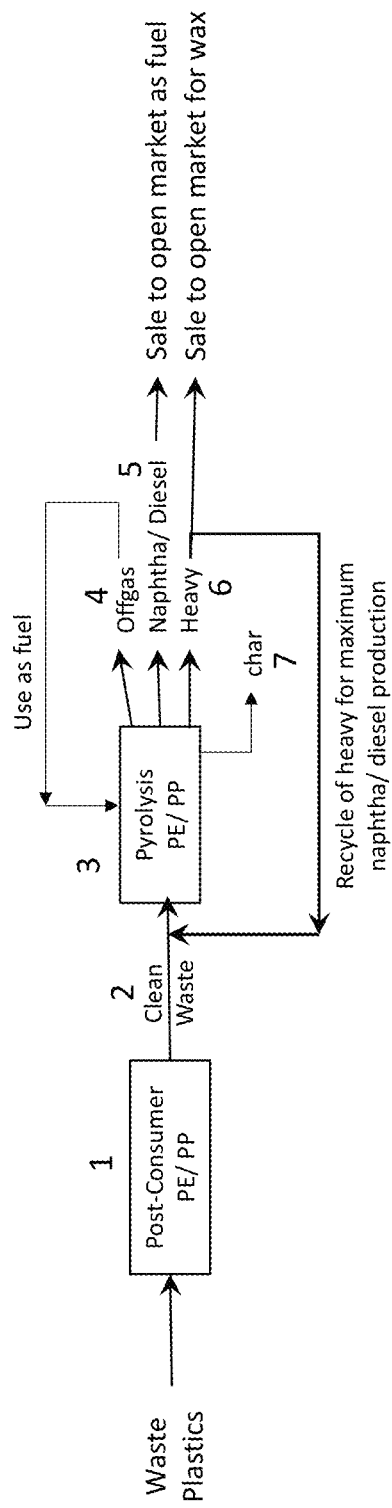
FIG. 1 depicts the current practice of pyrolyzing waste plastics to produce fuel or wax (base case).

In the present process, provided is a method to recycle waste polyethylene and/or polypropylene back to virgin polyethylene to establish a circular economy by combining distinct industrial processes. A substantial portion of polyethylene and polypropylene polymers are used in single use plastics and get discarded after its use. The single use plastic waste has become an increasingly important environmental issue. At the moment, there appear to be few options for recycling polyethylene and polypropylene waste plastics to value-added chemicals and fuel products. Currently, only a small amount of polyethylene/polypropylene is recycled via chemical recycling, where recycled and cleaned polymer pellets are pyrolyzed in a pyrolysis unit to make fuels (naphtha, diesel), steam cracker feed or slack wax.

Ethylene is the most produced petrochemical building block. Ethylene is produced in hundreds of millions of tons per year via steam cracking. The steam crackers use either gaseous feedstocks (ethane, propane and/or butane) or liquid feedstocks (naphtha or gas oil). It is a noncatalytic cracking process operating at very high temperatures, up to 850° C.

Polyethylene is used widely in various consumer and industrial products. Polyethylene is the most common plastic, over 100 million tons of polyethylene resins are produced annually. Its primary use is in packaging (plastic bags, plastic films, geomembranes, containers including bottles, etc.). Polyethylene is produced in three main forms: high-density polyethylene (HDPE, ~0.940-0.965 g/cm$^{-3}$), linear low-density polyethylene (LLDPE, ~0.915-0.940 g/cm$^{-3}$) and low-density polyethylene (LDPE, (<0.930 g/cm$^{-3}$), with the same chemical formula $(C_2H_4)_n$ but different molecular structure. HDPE has a low degree of branching with short side chains while LDPE has a very high degree of branching with long side chains. LLDPE is a substantially linear polymer with significant numbers of short branches, commonly made by copolymerization of ethylene with short-chain alpha-olefins.

Low density polyethylene (LDPE) is produced via radical polymerization at 150-300° C. and very high pressure of 1,000-3,000 atm. The process uses a small amount of oxygen and/or organic peroxide initiator to produce polymer with about 4,000-40,000 carbon atoms per the average polymer molecule, and with many branches. High density polyethylene (HDPE) is manufactured at relatively low pressure (10-80 atm) and 80-150° C. temperature in the presence of a catalyst. Ziegler-Natta organometallic catalysts (titanium(III) chloride with an aluminum alkyl) and Phillips-type catalysts (chromium(IV) oxide on silica) are typically used, and the manufacturing is done via a slurry process using a loop reactor or via a gas phase process with a fluidized bed reactor. Hydrogen is mixed with ethylene to control the chain length of the polymer. Manufacturing conditions of linear low-density polyethylene (LLDPE) are similar to those of HDPE except copolymerization of ethylene with short-chain alpha-olefins (1-butene or 1-hexene).

Today, only a small portion of spent polyethylene products is collected for recycling, due to the inefficiencies and ineffectiveness of the recycling efforts discussed above.

FIG. 1 shows a diagram of pyrolysis of waste plastics fuel or wax that is operated in the industry today. As noted above, generally, polyethylene and polypropylene wastes are sorted together 1. The cleaned polyethylene/polypropylene waste 2 is converted in a pyrolysis unit 3 to offgas 4 and pyrolysis oil (liquid product). The offgas 4 from the pyrolysis unit is used as fuel to operate the pyrolysis unit, and only the pyrolysis unit is used for commercial purposes. An on-site distillation unit separates the pyrolysis oil to produce naphtha and diesel 5 products which are sold to fuel markets. The heavy pyrolysis oil fraction 6 is recycled back to the pyrolysis unit 3 to maximize the fuel yield. Char 7 is removed from the pyrolysis unit 3. The heavy fraction 6 is rich in long chain, linear hydrocarbons, and is very waxy (i.e., forms paraffinic wax upon cooling to ambient temperature). Wax can be separated from the heavy fraction 6 and sold to the wax markets.

The present process converts pyrolyzed polyethylene and/or polypropylene waste plastic in large quantities by integrating the waste polymer pyrolysis product streams into an oil refinery operation. The resulting processes produce the feedstocks for the polymers (naphtha or $C_3$-$C_4$ for ethylene cracker), high quality gasoline and diesel fuel, and/or quality base oil.

Generally, the present process provides a circular economy for polyethylene plants. Polyethylene is produced via polymerization of pure ethylene. Clean ethylene can be made using a steam cracker. Either naphtha or a $C_3$-$C_4$ stream can be fed to the steam cracker. The ethylene is then polymerized to create polyethylene.

By adding refinery operations to upgrade the waste pyrolysis oil to higher value products (gasoline and diesel, base oil) and to produce clean LPG and naphtha for steam cracker for ultimate polyethylene polymer production, one is able to create positive economics for the overall process from recycled plastics to polyethylene product with quality identical to that of the virgin polymer.

A pyrolysis unit produces poor quality products containing contaminants, such as calcium, magnesium, chlorides, nitrogen, sulfur, dienes, and heavy components, which products cannot be used in large quantity for blending in transportation fuels. It has been discovered that by having these products go through the refinery units, the contaminants can be captured in pre-treating units and their negative impacts diminished. The fuel components can be further upgraded with appropriate refinery units with chemical conversion processes, with the final transportation fuels produced by the integrated process being of higher quality and meeting the fuels quality requirements. The present process will upgrade the wax into valuable lubricating base oil. The integrated process will generate a much cleaner naphtha stream for steam cracker feedstock for ethylene generation for polyethylene production. These large on-spec productions allow "cyclical economy" for the recycle plastics feasible.

The carbon in and out of the refinery operations are "transparent," meaning that all the molecules from the waste plastic do not necessarily end up in the exact olefin product cycled back to the polyolefin plants, but are nevertheless assumed as "credit" as the net "green" carbon in and out of the refinery is positive. With these integrated processes, the amount of virgin feeds needed for polyethylene plants will be reduced significantly.

Figure 2:
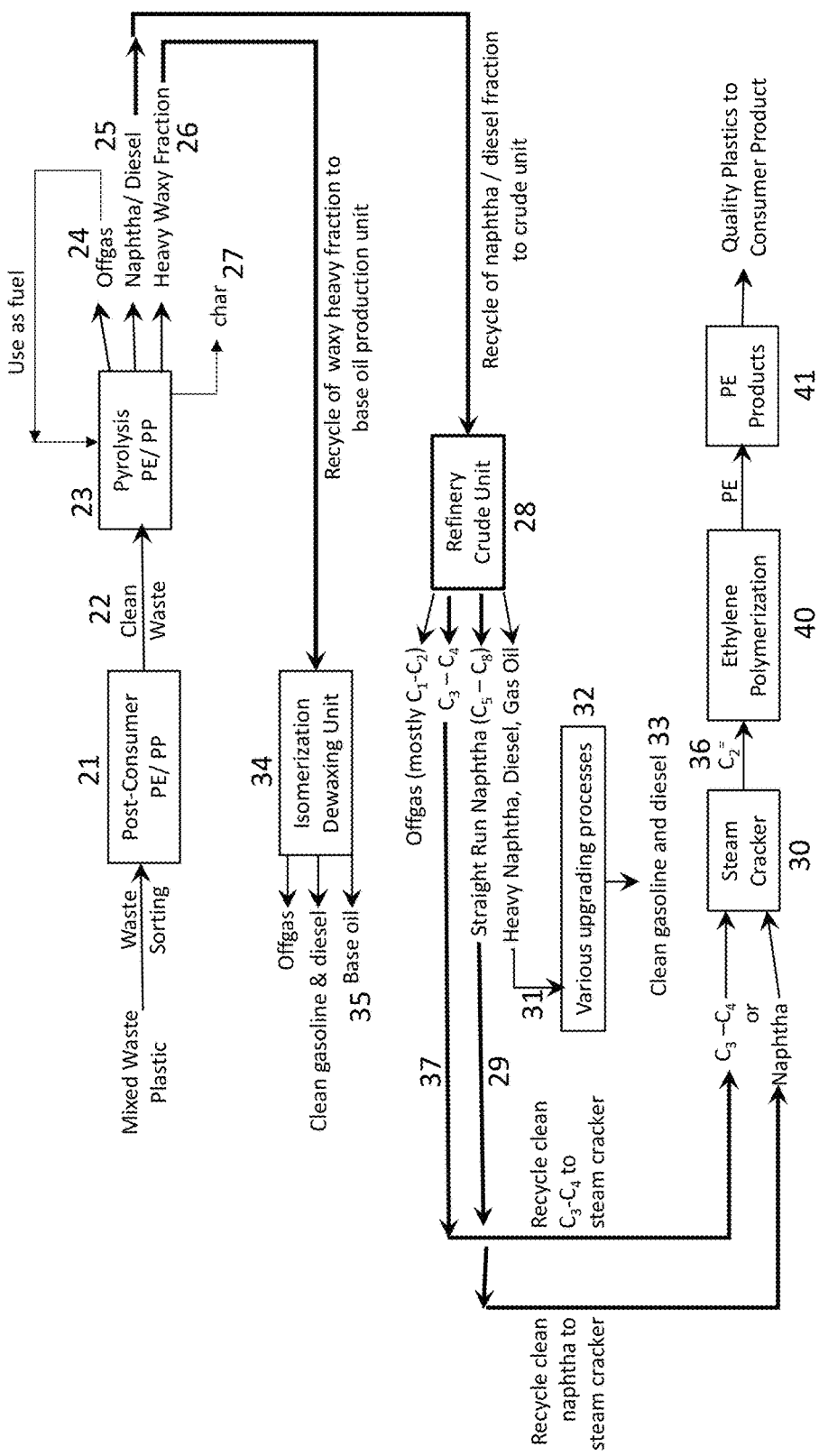
FIG. 2 depicts a present process for establishing a circular economy for waste plastics.

FIG. 2 shows the present integrated process, integrating refinery operations with recycle for effective polyethylene production. In FIG. 2, mixed waste plastics are sorted together 21. The cleaned waste plastic 22 is converted in a pyrolysis unit 23 to offgas 24 and a pyrolysis oil (liquid product) and optionally wax (solid product at ambient temperature). The offgas 24 from the pyrolysis unit can be used as fuel to operate the pyrolysis unit 23. The pyrolysis oil is separated, generally by an on-site distillation unit, into a naphtha/diesel fraction 25, and a heavy fraction 26. Char 27 is removed from the pyrolysis unit 23 after completion of the pyrolysis step.

The pyrolysis unit can be located near the waste plastics collection site, which site could be away from a refinery, near a refinery, or within a refinery. If the pyrolysis unit is located away from the refinery, then pyrolysis oil (naphtha/diesel and heavies) can be transferred to the refinery by truck, barge, rail car or pipeline. It is preferred, however, that the pyrolysis unit is within the waste plastics collection site or within the refinery.

Figure 3:
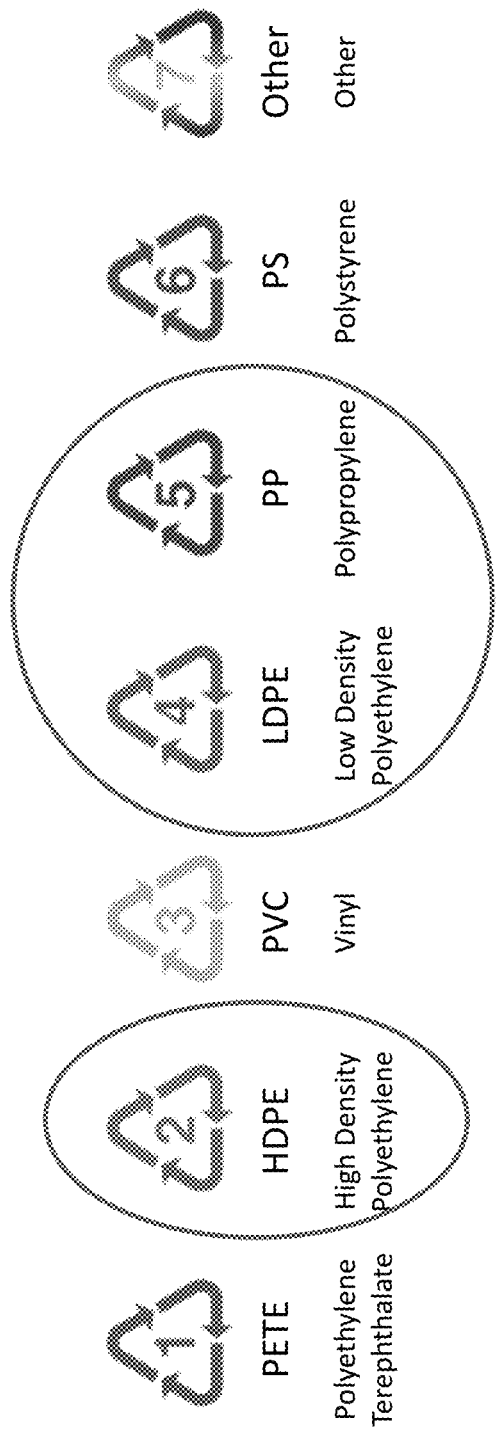
FIG. 3 depicts the plastic type classification for waste plastics recycling.

The preferred starting material for the present process is sorted waste plastics containing predominantly polyethylene and polypropylene (plastics recycle classification types 2, 4, and 5). The pre-sorted waste plastics are washed and shredded or pelleted to feed to a pyrolysis unit for thermal cracking. FIG. 3 depicts the plastic type classification for waste plastics recycling. Classification types 2, 4, and 5 are high density polyethylene, low density polyethylene and polypropylene, respectively. Any combination of the polyethylene and polypropylene waste plastics can be used. For the present process, at least some polyethylene waste plastic is preferred.

Proper sorting of waste plastics is very important in order to minimize contaminants such as N, Cl, and S. Plastics waste containing polyethylene terephthalate (plastics recycle classification type 1), polyvinyl chloride (plastics recycle classification type 3) and other polymers (plastics recycle classification type 7) need to be sorted out to less than 5%, preferably less than 1% and most preferably less than 0.1%. The present process can tolerate a moderate amount of polystyrene (plastics recycle classification type 6). Waste polystyrene needs to be sorted out to less than 30%, preferably less than 20% and most preferably less than 5%.

Washing of waste plastics removes metal contaminants such as sodium, calcium, magnesium, aluminum, and non-metal contaminants coming from other waste sources. Non-metal contaminants include contaminants coming from the Periodic Table Group IV, such as silica, contaminants from Group V, such as phosphorus and nitrogen compounds, contaminants from Group VI, such as sulfur compounds, and halide contaminants from Group VII, such as fluoride, chloride, and iodide. The residual metals, non-metal contaminants, and halides need to be removed to less than 50 ppm, preferentially less than 30 ppm and most preferentially to less than 5 ppm.

If the washing does not remove the metals, non-metal contaminants, and halide impurities adequately, then a separate guard bed can be used to remove the metals and non-metal contaminants.

The pyrolyzing is carried out by contacting a plastic material feedstock in a pyrolysis zone at pyrolysis conditions, where at least a portion of the feed(s) is cracked, thus forming a pyrolysis zone effluent comprising 1-olefins and n-paraffins. Pyrolysis conditions include a temperature of from about 400° C. to about 700° C., preferably from about 450° C. to about 650° C. Conventional pyrolysis technology teaches operating conditions of above-atmospheric pressures. See e.g., U.S. Pat. No. 4,642,401. Additionally, it has been discovered that by adjusting the pressure downward, the yield of a desired product can be controlled. See, e.g., U.S. Pat. No. 6,150,577. Accordingly, in some embodiments where such control is desired, the pyrolysis pressure is sub-atmospheric.

FIG. 2 shows the present integrated process where only the naphtha/diesel fraction 25 from the pyrolysis unit 23 is sent to a crude unit desalter 28 to produce $C_5$-$C_8$ naphtha 29, preferentially $C_5$-$C_7$ naphtha and most preferentially $C_5$-$C_6$ naphtha for the stream cracker 30 feed. The steam cracker 30 creates ethylene 36. The ethylene is passed to a polymerization unit 40 to produce polyethylene. The polyethylene is used for polyethylene consumer products 41.

The refinery will generally have its own hydrocarbon feed flowing through the refinery units. The flow volume of naphtha/diesel generated from the pyrolysis of waste plastic to the refinery units, here a crude unit, can comprise any practical or accommodating volume % of the total flow to the refinery units. Generally, the flow of the naphtha/diesel fraction generated from the waste plastic pyrolysis, for practical reasons, can be up to about 50 vol. % of the total flow, i.e., the refinery flow and the naphtha/diesel flow. In one embodiment, the flow of the naphtha/diesel is an amount up to about 20 vol. % of the total flow. In another embodiment, the flow of the naphtha/diesel is an amount up to about 10 vol. % of the total flow. About 20 vol. % has been found to be an amount that is quite practical in its impact on the refinery while also providing excellent results and being an amount that can be accommodated. The amount of naphtha/diesel generated from the pyrolysis can of course be controlled so that the fraction passed to the refinery units provides the desired volume % of the flow. Flow of the heavy wax fraction to the dewaxing unit can similarly be controlled and/or adjusted.

The refinery crude unit separates crude oil into multiple fractions such as liquefied petroleum gas (LPG), naphtha, kerosene, diesel and gas oil which will be further treated into useful petroleum products. The refinery crude unit has a crude treating section, commonly known as a desalter, and a crude oil distillation or fractionation section. The distillation section typically includes an atmospheric distillation unit and vacuum distillation unit.

The naphtha/diesel fraction from the pyrolysis unit is fed to the desalter to remove the salts and solids contained in the oil to protect downstream equipment from the harmful effects of the contaminants. To remove the salts, water is mixed with the oil and typically heated to temperatures between about 215° F. to about 280° F. and allowed to separate in the desalter unit.

Desalted oil is sent to an atmospheric distillation unit heated to about 340-372° C. (644-700° F.) at the bottom of the distillation column, and liquid is removed at various points of the fractional distillation column to produce various fuels. The fuels from the crude units are sent to various upgrading units in the refinery to remove impurities (nitrogen, sulfur) and to catalytically transform fractions to improve the product properties, such as octane and cetane numbers. The bottom residue from the atmospheric distillation column, also known as atmospheric residue, is sent to a vacuum distillation column to produce vacuum gas oil (650-1050° F.) and vacuum residue. The vacuum gas oil may be used to produce lubricating base oil or further cracked to produce gasoline, jet and diesel fuel.

The steam cracker and ethylene polymerization unit are preferably located near the refinery so that the feedstock (propane, butane, naphtha) can be transferred via pipeline. For a petrochemical plant located away from the refinery, the feedstock can be delivered via truck, barge, rail car or pipeline.

The heavy naphtha/diesel from the pyrolysis oil can be combined with hydrocarbon from the crude unit distillation and sent as a heavy naphtha, diesel, atmospheric gas oil stream 31 to appropriate refinery units 32 for upgrading into clean gasoline and diesel 33.

The heavy, waxy pyrolysis oil 26 from the pyrolysis unit is sent to a base oil dewaxing unit 34 with a precious metal containing zeolite catalyst for isomerization dewaxing or hydroisomerization to produce lubricating base oil 35 with excellent viscosity index and pour point. The flow of the heavy, waxy fraction can be controlled and adjusted as needed based upon the amount desired to be accommodated.

The isomerization dewaxing unit converts paraffinic, waxy heavy hydrocarbon material, typically boiling about 650° F., to high viscosity index (VI) lube oils. The unit typically comprises a feed hydrotreating section, isomerization dewaxing section, and distillation section.

The feed to the dewaxing unit is preferably subjected first to hydrogenation in a hydrotreating step. The hydrotreating occurs as part of the dewaxing unit. The feed to the hydrotreating step removes a significant portion of any nitrogen-containing, sulfur-containing, and/or oxygen-containing contaminants. The hydrotreating step also saturates portions of olefins, dienes and aromatics to improve the quality of the feed to the dewaxing unit. Typical hydrotreating conditions which are employed to remove contaminants while avoiding cracking include temperatures ranging from about 190° C. (374° F.) to about 340° C. (644° F.), pressure ranging from about 400 psig to about 3000 psig, space velocities (LHSV) in the range of about 0.1 $hr^{-1}$ to about 20 $hr^{-1}$, and hydrogen recycle rates ranging from about 400 to about 15,000 SCF/B. Hydrotreating catalysts include those conventionally used in hydrotreating units, containing metals such as Ni, Mo, Co, W and porous supports such as alumina, silica, or silica-alumina.

The hydrotreated heavy hydrocarbon is sent to the dewaxing reactor with an isomerization dewaxing catalyst which contains noble metal, intermediate pore size molecular sieve and binder. The catalyst preferably contains an intermediate pore size (10-membered ring) molecular sieve such as ZSM-23, ZSM-35, ZSM-48, ZSM-5, SSZ-32, SSZ-91, SAPO-11, SAPO-31 and SAPO-41. The noble metal includes Group VIII metals, such as Pt, Pd or mixture of Pt and Pd. Typically, porous alumina or silica is used to bind the material to produce catalyst pellets for the fixed bed reactor. Typical reaction conditions for the dewaxing reactor include temperature range of 200° C. (392° F.) to about 475° C. (887° F.), pressure ranging from about 200 psig to about 3000 psig, space velocities (LHSV) in the range of about 0.2 $hr^{-1}$ to about 10 $hr^{-1}$, and hydrogen recycle rates ranging from about 400 to about 15,000 SCF/B. The isomerization dewaxing catalyst converts n-paraffins to iso-paraffins, thereby reducing the pour point of the resulting oils and to form a high VI lube oil.

The effluent hydrocarbon from the isomerization dewaxing section is sent to a distillation unit to separate the effluent into various oil fractions, for example, a base oil fraction which boils above ~650° F., a diesel fraction which boils about 300-700° F., and a gasoline fraction boils which about 80-400° F. The boiling points for the gasoline, jet and diesel fractions will be adjusted depending on the season and local specifications.

In another embodiment, a $C_3$-$C_4$ fraction 37 is recovered from the refinery crude unit 28. The stream can also be fed to a steam cracker 30 for the production of ethylene 36. The ethylene can then be polymerized 40 and made into consumer products 41.

The benefits of a circular economy and an effective and efficient recycling campaign are realized by the present integrated process.

The following examples are provided to further illustrate the present process and its benefits. The examples are meant to be illustrative and not limiting.

Example 1: Properties of Pyrolysis Oil and Wax from Commercial Sources

Pyrolysis oil and wax samples were obtained from commercial sources and their properties are summarized in Table 1. These pyrolysis samples were prepared from waste plastics containing mostly polyethylene and polypropylene via thermal decomposition in a pyrolysis reactor at around 400-600° C., near atmospheric pressure without any added gas or a catalyst. A pyrolysis unit typically produces gas, liquid oil product, optionally wax product, and char. The pyrolysis unit's overhead gas stream containing thermally cracked hydrocarbon was cooled to collect condensate as pyrolysis oil (liquid at ambient temperature) and/or pyrolysis wax (solid at ambient temperature). The pyrolysis oil is the main product of the pyrolysis units. Some units produce pyrolysis wax as a separate product in addition to the pyrolysis oil.

TABLE 1

| Properties of As-Received Oil and Wax from Pyrolysis of Waste Plastics | | | | | |
|---|---|---|---|---|---|
| | Pyrolysis Oil Sample A | Pyrolysis Oil Sample B | Pyrolysis Oil Sample C | Pyrolysis Oil Sample D | Pyrolysis Wax Sample E |
| Specific Gravity at 60° F. | 0.814 | 0.820 | 0.774 | — | 0.828 |
| Simulated Distillation, ° F. | | | | | |
| 0.5% (Initial Boiling Point) | 87 | 299 | 18 | 86 | 325 |
| 5% | 179 | 306 | 129 | 154 | 475 |
| 10% | 214 | 309 | 156 | 210 | 545 |
| 30% | 322 | 346 | 285 | 304 | 656 |
| 50% | 421 | 447 | 392 | 421 | 733 |
| 70% | 545 | 585 | 517 | 532 | 798 |

TABLE 1-continued

Properties of As-Received Oil and Wax from Pyrolysis of Waste Plastics

|  | Pyrolysis Oil Sample A | Pyrolysis Oil Sample B | Pyrolysis Oil Sample C | Pyrolysis Oil Sample D | Pyrolysis Wax Sample E |
|---|---|---|---|---|---|
| 90% | 696 | 798 | 663 | 676 | 894 |
| 95% | 772 | 883 | 735 | 743 | 939 |
| 99.5% (Final Boiling Point) | 942 | 1079 | 951 | 888 | 1064 |
| *Carlo-Elba Hydrocarbon Analysis* | | | | | |
| Carbon, wt % | 87.6 | 84.21 | 85.46 | 85.97 | 85.94 |
| Hydrogen, wt % | 12.7 | 12.25 | 14.1 | 14.0 | 14.15 |
| Sum of C + H, wt % | 100.3 | 96.46 | 99.5 | 100.0 | 100.1 |
| H/C Molar Ratio | 1.73 | 1.75 | 1.98 | 1.96 | 1.98 |
| Bromine Number, g/100 g | 49 | 60 | 40 | 44 | 14 |
| *Hydrocarbon Type* | | | | | |
| Total Aromatics, vol % | 23.3 | 22.8 | 5.1 | 8.7 | 13.3 |
| Total Olefins & Naphthenes, vol % | 39.0 | 50.2 | 42.4 | 38.2 | 42.1 |
| Total Paraffins, vol % | 37.7 | 27 | 52.5 | 53.1 | 44.6 |
| *Contaminants* | | | | | |
| Total S, ppm | 48 | 29 | 7.8 | 99 | 6.3 |
| Total N, ppm | 751 | 1410 | 318 | 353 | 237 |
| Total Cl, ppm | 113 | 62 | 41 | 70 | 4.7 |
| O in naphtha & distillate, ppm | 250 | — | 574 | — | — |
| *Trace Elemental Impurities* | | | | | |
| Al, ppm | <1.1 | <0.56 | 0.6 | <0.53 | <0.68 |
| Ca, ppm | 1.4 | 11.5 | <0.5 | <0.53 | <0.68 |
| Fe, ppm | 4.9 | 11.9 | 1.6 | <1.1 | 3.1 |
| Mg, ppm | <0.51 | 1.3 | <0.52 | <0.53 | <0.68 |
| Na, ppm | 2.5 | <0.54 | <1.1 | <2.2 | <2.7 |
| Ni, ppm | <0.51 | <0.54 | <0.52 | 2 | <0.68 |
| V, ppm | <0.51 | <0.54 | <0.52 | 4 | <0.68 |
| P, ppm | 8.2 | 9.9 | <1.6 | <2.2 | 20.2 |
| Si, ppm | 82.5 | 49.6 | 13 | 17 | 3.1 |

ASTM D4052 method was used for specific gravity measurements. Simulated boiling point distribution curve was obtained using ASTM D2887 method. Carlo-Erba analysis for carbon and hydrogen was based on ASTM D5291 method. Bromine number measurement was based on ASTM D1159 method. Hydrocarbon-type analysis was done using a high resolution magnetic mass spectrometer using the magnet scanned from 40 to 500 Daltons. Total sulfur was determined using XRF per ASTM D2622 method. The nitrogen was determined using a modified ASTM D5762 method using chemiluminescence detection. The total chloride content was measured using combustion ion chromatography instrument using modified ASTM 7359 method. The oxygen content in naphtha and distillate boiling range was estimated using GC by GC/MS measurements with electron ionization detector for m/Z range of 29-500. Trace metal and non-metal elements in oil were determined using inductively coupled plasma-atomic emission spectrometry (ICP-AES).

Industrial pyrolysis process of sorted plastics, sourced predominantly from polyethylene and polypropylene waste, produced quality hydrocarbon streams with specific gravity ranging 0.7 to 0.9, and a boiling range from 18 to 1100° F. as in pyrolysis oil or pyrolysis wax.

The pyrolysis product is rather pure hydrocarbon made of mostly carbon and hydrogen. The hydrogen to carbon molar ratio varies from 1.7 to near 2.0. The Bromine Number is in the range of 14 through 60 indicating varying degrees of unsaturation coming from olefins and aromatics. The aromatic content is in the range of 5 to 23 volume % with a higher severity unit producing more aromatics. Depending on the process conditions of the pyrolysis unit, the pyrolysis products show paraffinic content ranging from mid-20 vol. % to mid-50 vol. %. The pyrolysis product contains a substantial amount of olefins. Samples A and B, pyrolysis oil produced under more severe conditions such as higher pyrolysis temperature and/or longer residence time, contain higher aromatic and lower paraffinic components, resulting H/C molar ratio of around 1.7 and high Bromine Number of 50-60. Samples C and D were produced at less severe conditions, and the pyrolysis oils are more paraffinic, resulting H/C molar ratio of close to 2.0 and Bromine Number around 40. Sample E, pyrolysis wax, is mostly paraffinic, saturated hydrocarbon with a substantial amount of normal hydrocarbons (as opposed to branched hydrocarbons) with low Bromine Number of only 14.

The following Examples 2 through 5 show the evaluation of waste plastics pyrolysis oil for transportation fuel.

Example 2: Fractionation of Pyrolysis Oil for Evaluation as Transportation Fuel

Sample D was distilled to produce hydrocarbon cuts representing gasoline (350° F.$^-$), jet (350-572° F.), diesel (572-700° F.) and the heavy (700° F.$^+$) fractions. Table 2 summarizes the boiling point distribution and impurity distributions among the distilled product fractions.

TABLE 2

Distillation of Pyrolysis Oil into Fuel Fractions

| Sample ID | Sample D | Sample F | Sample G | Sample H | Sample I |
|---|---|---|---|---|---|
| Intended Fraction | | Gasoline Cut | Jet Cut | Diesel Cut | Unconverted |
| Cut Point Target, °F. | | 350⁻ | 350-572 | 572-700 | 700⁺ |
| Distillation Actual Yields, wt % | | 37.2 | 38.0 | 15.0 | 9.3 |
| Simulated Distillation, F | | | | | |
| IBP (0.5 wt %) | 86 | 27 | 299 | 539 | 640 |
| 5 wt % | 154 | 98 | 345 | 557 | 684 |
| 10 wt % | 210 | 147 | 365 | 574 | 696 |
| 30 wt % | 304 | 222 | 416 | 597 | 727 |
| 50 wt % | 421 | 270 | 457 | 619 | 758 |
| 70 wt % | 532 | 291 | 492 | 644 | 808 |
| 90 wt % | 676 | 337 | 546 | 674 | 898 |
| 95 wt % | 743 | 347 | 554 | 683 | 953 |
| FBP (99.5 wt %) | 888 | 385 | 591 | 711 | 1140 |
| Total S, ppm | 99 | 52 | 35 | 80 | 320 |
| Total N, ppm | 353 | 215 | 556 | 232 | 467 |
| Total Cl, ppm | 70 | 181 | 27 | 12 | 13 |

Example 3: Evaluation of Pyrolysis Oil Cut for Gasoline Fuel

Sample F, a pyrolysis oil cut for gasoline fuel boiling range, was evaluated to assess its potential to use as gasoline fuel. Sample F has the carbon number range of C5-C12, typical of the gasoline fuel.

Due to the olefinic nature of the pyrolysis oil, oxidation stability (ASTM D525) and gum forming tendency (ASTM D381) were identified as the most critical properties to examine. Research octane number (RON) and motor octane number (MON) are also the critical properties for engine performance. The RON and MON values were estimated from detailed hydrocarbon GC analysis.

TABLE 3

Evaluation of Pyrolysis Oil Naphtha Fraction for Gasoline Fuel

| | Oxidation Stability, mm | Washed Gum, mg/100 mL | RON | MON |
|---|---|---|---|---|
| Sample F | 90 | 5.0 | 71.4 | 67.7 |
| Reference gasoline | >1440 | 1 | 95.8 | 86.2 |
| 4/96 vol. % Blend of Sample F with reference gasoline | >1440 | 2.0 | 94.5 | 85.1 |
| 15/85 vol. % Blend of Sample F with reference gasoline | >1440 | 2.2 | 91.8 | 83.1 |

Sample F, a pyrolysis oil cut for gasoline fuel boiling range, cannot be used by itself as automotive gasoline fuel due to its poor quality. The gasoline fraction from the pyrolysis oil showed very poor oxidation stability in that Sample F failed only after 90 min compared to the target stability of longer than 1440 minutes. The pyrolysis gasoline exceeded the wash gum target of 4 mg/100 mL suggesting severe gum forming tendency. The pyrolysis gasoline has poor octane numbers compared to the reference gasoline. A premium unleaded gasoline was used as the reference gasoline.

We also examined the potential of blending of the pyrolysis gasoline cut for a limited amount to the reference gasoline. Our study showed that possibly up to 15 volume % of Sample F can be blended to the refinery gasoline while still meeting the fuels property targets. By integrating the pyrolysis gasoline product with a refinery fuel, the overall product quality can be maintained.

These results indicate that the as-produced gasoline fraction of pyrolysis oil has limited utility as gasoline fuel. Upgrading in a refinery unit is preferred to convert this gasoline fraction of the pyrolysis oil into hydrocarbon that meets the gasoline fuel property targets.

Example 4: Evaluation of Pyrolysis Oil Cut for Jet Fuel

Sample G, a pyrolysis oil cut for jet fuel boiling range, was evaluated to assess its potential to use as jet fuel. Sample G has the carbon number range of C9-C18, typical of the jet fuel.

Due to the olefinic nature of the pyrolysis oil, jet fuel thermal oxidation test (D3241) was considered as the most critical test. The pyrolysis oil jet cut as-is, Sample G, had only 36 minutes of oxidation stability suggesting the pure pyrolysis jet cut is unsuitable for use as jet fuel.

We prepared a 5 volume % blend of pyrolysis jet cut (Sample G) with refinery produced jet. The blend still failed for the jet fuel oxidation test as shown in Table 4.

TABLE 4

Evaluation of Pyrolysis Oil Jet Fraction for Jet Fuel

| | Jet Fuel Thermal Oxidation Test |
|---|---|
| Reference jet fuel | Passed |
| 5/95 vol. % Blend of Sample G with reference jet fuel | Failed |

These results indicate that the as-produced jet fraction of pyrolysis oil is completely unsuitable for jet fuel, and upgrading in a refinery unit is required to convert this jet fraction of the pyrolysis oil into hydrocarbon that meets the jet fuel property targets.

Example 5: Evaluation of Pyrolysis Oil Cut for Diesel Fuel

Sample H, a pyrolysis oil cut for diesel fuel boiling range, was evaluated to assess its potential to use as diesel fuel. Sample H has the carbon number range of C14-C24, typical of the diesel fuel.

Sample H contains a substantial amount of normal hydrocarbons. Since normal hydrocarbons tends to exhibit waxy characteristics, cold flow properties such as pour point (ASTM D5950-14) and cloud points (ASTM D5773) were considered as the most critical tests.

We prepared two blends at 10 and 20 volume % of Sample H with refinery produced diesel fuel. However, both blends still failed for the target pour point of less than −17.8° C. (0° F.) pour points.

TABLE 5

Evaluation of Pyrolysis Oil Diesel Fraction for Diesel Fuel

| | Cloud Point (° C.) | Pour Point (° C.) | Pour Point Test |
|---|---|---|---|
| Reference diesel fuel | −17.1 | −19.0 | Passed |
| 10/90 vol. % Blend of Sample H with reference diesel fuel | −11.1 | −12.0 | Failed |
| 20/80 vol. % Blend of Sample H with reference diesel fuel | −5.5 | −7.0 | Failed |

These results indicate that the pyrolysis oil as-is is completely unsuitable for diesel fuel, and upgrading in a refinery unit is required to covert the diesel fraction of pyrolysis oil into hydrocarbon that meets the diesel fuel property targets.

Examples 6: Coprocessing of Pyrolysis Oil to Crude Unit or Desalter Unit

Results from Table 1 showed that industrial pyrolysis process of sorted plastics, sourced predominantly from polyethylene and polypropylene waste, produced quality pyrolysis oil made of mostly carbon and hydrogen. With good sorting and efficient pyrolysis unit operation, the nitrogen and sulfur impurities are at low enough levels that a modern refinery can handle cofeeding of pyrolysis feedstocks to their processing units with no detrimental impacts.

However, some pyrolysis oils may still contain high amounts of metals (Ca, Fe, Mg) and other non-metals (N, S, P, Si, Cl, O) that could negatively affect the performance of conversion units in a refinery. For pyrolysis oil products with high impurity levels are preferentially fed to a desalter unit before by the crude unit so that bulk of impurities are removed effectively by the desalter.

By feeding the pyrolysis feedstock to a crude unit or to a desalter unit before the crude unit, the pyrolysis oil will be fractionated into multiple components and then converted in the subsequent conversion units including paraffin isomerization unit, jet hydrotreating unit, diesel hydrotreating unit, fluid catalytic cracking unit (FCC), alkylation unit, hydrocracking unit and/or coker unit to make gasoline, jet and diesel fuel with satisfactory product properties. The conversion units (FCC or hydrocracking unit) will also convert the heavy cut (corresponding to Sample I) into quality transportation fuels.

After the crude unit, the pyrolysis oil will be converted further in the subsequent conversion units. The following Example 7 demonstrates the conversion of waste plastics pyrolysis oil into quality transportation fuel in a refinery conversion unit, using a FCC unit as an example.

Example 7: Conversion of Pyrolysis Oil in FCC

To study the impact of coprocessing of waste plastics pyrolysis oil to FCC, series of laboratory tests were carried out with Samples A and C. Vacuum gas oil (VGO) is the typical feed for FCC. FCC performances of 20% blend of pyrolysis oil with VGO and pure pyrolysis oil were compared with that of the pure VGO feed.

The FCC experiments were carried out on a Model C ACE (advanced cracking evaluation) unit fabricated by Kayser Technology Inc. using regenerated equilibrium catalyst (Ecat) from a refinery. The reactor was a fixed fluidized reactor using $N_2$ as fluidization gas. Catalytic cracking experiments were carried out at the atmospheric pressure and 900° F. reactor temperature. The cat/oil ratio was varied between 5 to 8 by varying the amount of the catalyst. A gas product was collected and analyzed using a refinery gas analyzer (RGA), equipped with GC with FID detector. In-situ regeneration of a spent catalyst was carried out in the presence of air at 1300° F., and the regeneration flue gas was passed through a LECO unit to determine the coke yield. A liquid product was weighted and analyzed in a GC for simulated distillation (D2887) and $C_5^-$ composition analysis. With a material balance, the yields of coke, dry gas components, LPG components, gasoline (C5-430° F.), light cycle oil (LCO, 430-650° F.) and heavy cycle oil (HCO, 650° F.$^+$) were determined. The results are summarized below in Table 6.

TABLE 6

Evaluation of Pyrolysis Oil Cofeeding to FCC

| Feed | 100% VGO | 20/80 vol % blend, Sample A/VGO | 20/80 vol % blend, Sample C/VGO | 100% Sample A | 100% Sample C |
|---|---|---|---|---|---|
| Cat/Oil, wt/wt | 6.0 | 6.0 | 6.0 | 6.0 | 6.0 |
| Conversion, wt %* | 81.3 | 83.15 | 83.09 | 76.1 | 78.82 |

TABLE 6-continued

Evaluation of Pyrolysis Oil Cofeeding to FCC

| Feed | 100% VGO | 20/80 vol % blend, Sample A/VGO | 20/80 vol % blend, Sample C/VGO | 100% Sample A | 100% Sample C |
|---|---|---|---|---|---|
| WLP Impurity** | | | | | |
| Total O, ppm | 81 | 76 | 62 | 54 | 67 |
| Total N, ppm | 27 | 30 | 33 | 50 | 21 |
| Yields | | | | | |
| Coke, wt % | 4.45 | 4.35 | 4.20 | 3.56 | 2.90 |
| Total Dry Gas, wt % | 2.08 | 1.96 | 1.93 | 1.55 | 1.43 |
| Hydrogen | 0.16 | 0.12 | 0.12 | 0.05 | 0.04 |
| Methane | 0.68 | 0.65 | 0.64 | 0.50 | 0.46 |
| Ethane | 0.44 | 0.43 | 0.41 | 0.33 | 0.28 |
| Ethylene | 0.76 | 0.74 | 0.72 | 0.63 | 0.61 |
| Total LPG, wt % | 21.25 | 21.08 | 21.50 | 20.17 | 24.40 |
| Propane | 1.78 | 1.76 | 1.72 | 1.47 | 1.53 |
| Propylene | 5.53 | 5.51 | 5.56 | 5.57 | 6.75 |
| n-Butane | 1.56 | 1.56 | 1.54 | 1.29 | 1.34 |
| Isobutane | 6.61 | 6.48 | 6.64 | 5.43 | 6.61 |
| C4 olefins | 5.77 | 5.77 | 6.04 | 6.41 | 8.16 |
| Gasoline, wt % | 53.53 | 55.75 | 55.46 | 62.53 | 61.75 |
| LCO, wt % | 12.89 | 12.23 | 11.93 | 10.37 | 8.03 |
| HCO, wt % | 5.81 | 4.63 | 4.98 | 1.82 | 1.50 |
| Octane Number*** | 88.05 | 84.57 | 82.79 | 73.75 | 75.41 |

*Conversion—conversion of 430° F.$^+$ fraction to 430° F.$^-$
**Impurity level of N and O in whole liquid product in fuels boiling range by GC x GC, ppm
***Octane number, (R + M)/2, was estimated from detailed hydrocarbon GC of FCC gasoline.

The results in Table 6 show that up to 20 volume % cofeeding of pyrolysis oil only makes very slight changes in the FCC unit performance indicating coprocessing of pyrolysis oil up to 20% is readily feasible. The 20 volume % blending of Sample A or Sample C led to very slight reduction of coke and dry gas yields, slight increase in gasoline yield and slight decrease in LCO and HCO, which are favorable in most situations. With paraffinic nature of pyrolysis oil, the 20% blends of A and C lowered the Octane number by about 3-5 numbers. With refinery operational flexibility, these octane number debits can be compensated with blending or feeding location adjustments.

The FCC unit cracks the pyrolysis oil info fuel range hydrocarbons, reduces impurities, and isomerize n-paraffins to isoparaffins. All these chemistry will improve the fuel properties of the pyrolysis oil and wax. By cofeeding the pyrolysis oil through the FCC process unit with a zeolite catalyst, the oxygen and nitrogen impurities in the fuel range were reduced substantially, from about 300-1400 ppm N to about 30 ppm N and from about 250-540 ppm 0 to about 60-80 ppm O. The hydrocarbon composition of all these cofeeding products are well within the typical FCC gasoline range.

The FCC runs of 100% pyrolysis oil showed substantial debits of Octane numbers by about 13-14 numbers. This shows that coprocessing of pyrolysis oil is preferred over processing of pure 100% pyrolysis oil.

Example 8: Generation of $C_3$-$C_4$ and Naphtha Feedstocks for Chemicals Production Via Cofeeding of Waste Plastics Pyrolysis Product to Refinery Crude Unit By feeding of the pyrolysis oil to a crude unit or to a desalter unit before the crude unit, the pyrolysis oil will be fractionated into multiple components. With the pyrolysis oil cofeeding, the refinery crude unit produces substantial amounts of clean propane, butane, and naphtha streams with recycle contents that can be fed to a steam cracker. At least a portion of the streams, if not all, are fed to the steam cracker.

Example 9: Feeding of Recycled $C_3$-$C_4$ and/or Naphtha to Steam Cracker for Ethylene Production, Followed by Production of Circular Polyethylene Resin and Polyethylene Consumer Products The propane, butane and naphtha streams produced via cofeeding of pyrolysis products to a crude unit per Example 8 are good feedstock to cofeed to a steam cracker for production of ethylene with a recycle content. The ethylene is then processed in a polymerization unit to produce polyethylene resin containing some recycled-polyethylene/polypropylene derived materials while the quality of the newly produced polyethylene is indistinguishable to the virgin polyethylene made entirely from virgin petroleum resources. The polyethylene resin with the recycled material is then further processed to produce various polyethylene products to fit the needs of consumer products. These polyethylene consumer products now contain chemically recycled, circular polymer while qualities of the polyethylene consumer products are indistinguishable from those made entirely from virgin polyethylene polymer. These chemically recycled polymer products are different from the mechanically recycled polymer products whose qualities are inferior to the polymer products made from virgin polymers.

Examples 10: Coprocessing of Pyrolysis Wax to Isomerization Dewaxing Unit to Produce Lubricating Base Oil Results from Table 1 showed that industrial pyrolysis process of sorted plastics, sourced predominantly from polyethylene and polypropylene waste, produced pyrolysis wax made of mostly carbon and hydrogen. Various process options were examined for making lubricating base oil from the pyrolysis wax via hydroisomerization dewaxing process.

The pyrolysis wax still contain too high amounts of nitrogen and sulfur impurities, metals (Ca, Fe, Mg) and other non-metals (P, Si, Cl, O) that negatively affect the performance of the hydroisomerization dewaxing catalyst containing precious metal (Pt, Pd, or a combination of Pt and Pd) and a zeolite such as ZSM-11, ZSM-23, ZSM-48, SSZ-32, SSZ-91, SAPO-11, SAPO-31 and SAPO-41.

An attempt to make quality lubricating base oil by direct feeding of pure pyrolysis oil using a dewaxing catalyst was not successful, as shown below in Example 11. To maintain the catalyst activity, for direct feeding of pyrolysis wax to the hydroisomerization dewaxing unit, the cofeeding level needs to be limited less than 10 vol. %, preferentially less than 5 vol. %. The volume percent limitation is likely coming from the nitrogen impurity which is detrimental to the zeolite activity. The nitrogen level of the combined feed needs to be maintained at less than 5 ppm nitrogen, preferentially less than 1 ppm nitrogen.

Alternatively, the pyrolysis wax is cofed to a hydrocracking unit to remove S, N, and other impurities. The hydrocracking unit hydrogenates the pyrolysis wax and removes impurities. The hydrocracking unit severity may be adjusted to maximize the base oil yield of the combined feed. Cofeeding level to the hydrocracking unit can be as much as 50 vol. %, preferentially 20 vol. %. In this case, the volume percent limitation may come from the metals impurity or N impurity or P impurity depending on the unit configuration and the catalyst choice. The bottom fraction (650° F.$^+$) containing hydrocracked pyrolysis wax is then fed to the hydroisomerization dewaxing unit to make a lubricating base oil. Alternatively, the pyrolysis wax is fed to a dedicated hydrogenation unit to remove S, N, and other impurities before fed to the hydroisomerization dewaxing unit to make a base oil. The hydrogenation step removes impurities very easily, as shown in Example 12 below. The hydrotreated wax can be cofed to the hydroisomerization dewaxing at any volume percent.

The following Examples 11 and 12 demonstrate an unsuccessful route and a successful process route of making quality base oil in refinery conversion units using waste plastics pyrolysis wax as the feedstock.

Example 11: Production of Base Oil from Recycled Pyrolysis Wax Via Hydroisomerization Dewaxing Process Only To assess the potential of base oil production from the recycled wax, Sample E, crude pyrolysis wax, was vacuum distilled to produce 690° F.$^+$ fraction, Sample J. 100% Sample J was hydroisomerized in a batch autoclave unit with a Pt/SSZ-32/Alumina catalyst overnight at an oil to catalyst weight ratio of 10:1, at 650° F. and under 800 psig H$_2$ pressure. The hydrogenated product was vacuum distilled to produce 690° F.$^+$ boiling and clear oil, Sample K. Properties of the samples are summarized in Table

TABLE 7

Hydroisomerization/Dewaxing of Pyrolysis Wax with Pt/Zeolite Catalyst

| | Sample E | Sample J, Slack Wax | Sample K, Dewaxed oil |
|---|---|---|---|
| Description | As-received pyrolysis wax | 690° F$^+$ wax cut of Sample E | 690° F$^+$ oil from dewaxing of Sample J followed by distillation |
| Simulated Distillation, ° F. | | | |
| 0.5% (Initial Boiling Point) | 325 | 680 | 694 |
| 5% | 475 | 715 | 727 |
| 10% | 545 | 727 | 742 |
| 30% | 656 | 768 | 783 |
| 50% | 733 | 807 | 820 |
| 70% | 798 | 854 | 865 |
| 90% | 894 | 930 | 939 |
| 95% | 939 | 970 | 980 |
| 99.5% (Final Boiling Point) | 1064 | 1067 | 1096 |
| Bromine Number, g/100 g | 14 | 6 | <0.1 |
| Contaminants | | | |
| Total S, ppm | 6.3 | — | — |
| Total N, ppm | 237 | 180 | <0.3 |
| Total Cl, ppm | 4.7 | 1.9 | — |
| Trace Elemental Impurities | | | |
| Fe, ppm | 3.1 | 3.0 | <1.1 |
| P, ppm | 20.2 | 32.5 | <0.55 |
| Si, ppm | 3.1 | <2.7 | <2.2 |
| Color & physical state | Light brown solid | Light brown solid | Clear liquid |
| Viscosity Index (VI) | — | 169 | 162 |
| Viscosity at 100° C., cSt | — | 4.26 | 4.67 |
| Viscosity at 70° C., cSt | — | 7.52 | — |
| Viscosity at 40° C., cSt | — | — | 19.81 |
| Pour Point, ° C. | 42 | — | 12 |
| Cloud Point, ° C. | — | — | 20 |

Sample J, 690° F.$^+$ cut slack wax from waste plastic pyrolysis, is low-viscosity wax at ~4.3 cSt at 100° C. with an excellent viscosity index of 169. However, the slack wax contains significant amounts of N (180 ppm) and P (32.5 ppm) which will passivate the zeolite catalyst activity in the hydroisomerization dewaxing process. Sample K, dewaxed and distilled oil, showed viscosity index of 162 and the pour point of 12° C. Even though the pour point was reduced substantially from 42° C. of Sample E, the pour point of 12°

C. is still very poor relative to the industry target of −15° C. or below. This oil cannot be used for high performance modern lubricant as this oil will lose fluid/oily characters when the ambient temperature drops below 12° C. and the oil will become thick or solid-like material.

This study indicates that pyrolysis wax needs to be hydrotreated or hydrocracked to reduce the N impurity and other impurities in order to produce an acceptable base oil from a waste plastics pyrolysis wax.

Example 12: Production of Quality Base Oil with Recycle Content by Hydrotreating Followed by Hydroisomerization Dewaxing Process Sample E, crude pyrolysis wax, was hydrogenated in a continuous fixed bed unit containing a NiMo/Alumina catalyst at 625° F. reactor temperature and 1200 psig pressure. A liquid feed flow rate of 1.5 hr$^{-1}$ relative to the catalyst bed volume and H₂/Hydrocarbon flow rate of 2500 scf/bbl were used to produce the hydrogenated product, which is mostly wax. The hydrogenated product was vacuum distilled to produce 650° F.+ fraction as a hydrogenated pyrolysis paraffin wax, Sample L.

Sample L, hydrogenated wax made from waste plastics pyrolysis, was subjected to hydroisomerization dewaxing in a continuous fixed bed unit containing a Pt/ZZS-91/Alumina catalyst at 625° F. reactor temperature and 400 psig pressure. A liquid feed flow rate of 1.0 hr$^{-1}$ relative to the catalyst bed volume and H₂/Hydrocarbon flow rate of 2500 scf/bbl were used to produce the dewaxed oil. The dewaxed oil was vacuum distilled to produce 690° F.+ fraction as the final dewaxed base oil product, Sample M. The results are summarized in Table 8.

TABLE 8

Hydrotreating/Dewaxing of Pyrolysis Wax for Base Oil Production
Hydrogenation and Dewaxing of Pyrolysis Wax with Pt/Zeolite Catalyst for Lubricating Base Oil Production

| Description | Sample E | Sample L, Hydrogenated Wax | Sample M, Dewaxed oil |
|---|---|---|---|
| | As-received pyrolysis wax | Hydrogenated Sample E, cut at 650° F.+ | Dewaxed Sample L, cut at 690° F.+ |
| Simulated Distillation, ° F. | | | |
| 0.5% (Initial Boiling Point) | 325 | 625 | 651 |
| 5% | 475 | 671 | 681 |
| 10% | 545 | 686 | 695 |
| 30% | 656 | 735 | 738 |
| 50% | 733 | 781 | 782 |
| 70% | 798 | 834 | 836 |
| 90% | 894 | 917 | 923 |
| 95% | 939 | 958 | 965 |
| 99% (Final Boiling Point) | 1033 | 1041 | 1048 |
| Bromine Number, g/100 g | 14 | <0.09 | — |
| Contaminants | | | |
| Total S, ppm | 6.3 | Below detection | — |
| Total N, ppm | 237 | <0.4 | — |
| Total Cl, ppm | 4.7 | Below detection | — |
| Trace Elemental Impurities | | | |
| Fe, ppm | 3.1 | <1.1 | — |
| P, ppm | 20.2 | <2.2 | — |
| Si, ppm | 3.1 | <2.7 | — |
| Color & physical state | Light brown solid | White solid | Clear liquid |
| Viscosity Index | — | 163 | 135 |
| Viscosity at 100° C., cSt | — | 3.80 | 4.05 |
| Viscosity at 70° C., cSt | — | 6.66 | — |
| Viscosity at 40° C., cSt | — | — | 17.39 |
| Pour Point, ° C. | 42 | 51 | −35 |
| Cloud Point, ° C. | — | — | −17 |

Hydrogenation of pyrolysis wax, Sample E, produced excellent quality hydrogenated wax, Sample L. All trace impurities are completely removed upon hydrogenation in that Sample L has no measurable impurities that could harm the dewaxing catalyst. This example shows that high quality, pure paraffinic wax can be produced effectively from waste plastic containing predominately polyethylene, polypropylene and that mild hydrogenation is a very effective method to purify the waste plastic derived wax.

Hydroisomerization dewaxing of the hydrogenated wax (Sample L) produced remarkably excellent quality 4 cSt base oil with viscosity index of 135, pour point of −35° C. and cloud point of −17° C. (Sample M). In terms of the quality, this base oil made from waste plastics pyrolysis falls in the Group III base oil category. These positive results were quite surprising considering the poor property observed with Sample K. Low viscosity 4 cSt base oil is highly desirable as it is widely used as a component in automotive lubricants.

The Examples 11 and 12 clearly show that excellent quality base oil can be made from the wax derived from pyrolysis of polyethylene and polypropylene waste with careful selection of cofeeding process configuration and process conditions. The results clearly show that the preferred way to make a base oil from a waste plastics pyrolysis wax is by hydrogenation followed by hydroisomerization dewaxing process. The final base oil produced has a recycle content, and the quality of the base oil is comparable or superior to that of base oil produced by the conventional refinery processing with virgin crude oil.

The foregoing examples together clearly show a new effective way to recycle a large quantity of polyethylene and polypropylene derived waste plastics via chemical recycling through pyrolysis followed by cofeeding of the pyrolysis products in a refinery via efficient integration. This integration allows quality fuels, lubricating base oil and circular polymer productions.

As used in this disclosure the word "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the composition. The phrase "consisting of" or "consists of" is intended as a transition meaning the exclusion of all but the recited elements with the exception of only minor traces of impurities.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise that as specifically described without actually departing from the spirit and scope of the present invention as defined by the appended claims.

What is claimed is:

1. A continuous process for converting waste plastic into recycle for polyethylene polymerization comprising:
   (a) selecting waste plastics containing polyethylene and/or polypropylene;
   (b) passing the waste plastics from (a) through a pyrolysis reactor to thermally crack at least a portion of the waste plastics and produce a pyrolyzed effluent;
   (c) separating the pyrolyzed effluent into offgas, a naphtha/diesel fraction, a heavy fraction, and char;
   (d) passing the naphtha/diesel fraction to a crude unit in a refinery;
   (e) recovering a straight run naphtha ($C_5$-$C_8$) fraction from the crude unit;
   (f) passing the straight run naphtha fraction ($C_5$-$C_8$) to a steam cracker for ethylene production; and
   (g) passing the heavy fraction to an isomerization dewaxing unit to produce a base oil.

2. The process of claim 1, wherein the naphtha/diesel fraction of (c) is passed directly to a refinery crude unit and contaminants are removed in a crude unit desalter.

3. The process of claim 1, wherein contaminants are removed at the pyrolysis reactor.

4. The process of claim 1, wherein the ethylene produced in (f) is subsequently polymerized.

5. The process of claim 4, wherein consumer polyethylene products are prepared from the polymerized ethylene.

6. The process of claim 1, wherein the waste plastics selected in (a) are from plastics classification group 2, 4, and/or 5.

7. The process of claim 1, wherein heavy naphtha/diesel/atmospheric gas oil is recovered from the crude unit and further processed in the refinery to clean gasoline, diesel, or jet fuel.

8. The process of claim 1, wherein virgin crude oil is passed to the crude unit and the amount of virgin crude oil processed by the crude unit is reduced due to the naphtha/diesel fraction passed to the crude unit.

9. The process of claim 1, wherein the amount of base oil produced by the isomerization dewaxing unit is increased due to the naphtha/diesel fraction passed to the crude unit.

10. The process of claim 1, wherein the heavy fraction in (g) is hydrotreated and then isomerized in the dewaxing unit.

11. The process of claim 1, wherein the volume flow of the naphtha/diesel fraction to the crude unit in the refinery comprises up to about 50 volume % of the total hydrocarbon flow to the crude unit.

12. The process of claim 11, wherein the naphtha/diesel flow comprises up to 20 volume %.

13. A continuous process for converting waste plastic into recycle for polyethylene polymerization comprising:
   (a) selecting waste plastics containing polyethylene and/or polypropylene;
   (b) passing the waste plastics from (a) through a pyrolysis reactor to thermally crack at least a portion of the waste plastics and produce a pyrolyzed effluent;
   (c) separating the pyrolyzed effluent into offgas, a naphtha/diesel fraction, a heavy fraction, and char;
   (d) passing the naphtha/diesel fraction to a crude unit in a refinery;
   (e) recovering a propane and butane ($C_3$-$C_4$) fraction from the crude unit;
   (f) passing the ($C_3$-$C_4$) fraction to a steam cracker for ethylene production; and
   (g) passing the heavy fraction to an isomerization dewaxing unit to produce a base oil.

14. The process of claim 13, wherein the naphtha/diesel fraction of (c) is passed directly to a refinery crude unit and contaminants are removed in a crude unit desalter.

15. The process of claim 13, wherein contaminants are removed at the pyrolysis reactor.

16. The process of claim 13, wherein the ethylene produced in (f) is subsequently polymerized.

17. The process of claim 16, wherein consumer polyethylene products are prepared from the polymerized ethylene.

18. The process of claim 13, wherein the waste plastics selected in (a) are from plastics classification group 2, 4, and/or 5.

19. The process of claim 13, wherein heavy naphtha/diesel/atmospheric gas oil is recovered from the crude unit and further processed in the refinery to clean gasoline, diesel, or jet fuel.

20. The process of claim 13, wherein virgin crude oil is passed to the crude unit and the amount of virgin crude oil processed by the crude unit is reduced due to the naphtha/diesel fraction passed to the crude unit.

21. The process of claim 13, wherein the amount of base oil produced by the isomerization dewaxing unit is increased due to the naphtha/diesel fraction passed to the crude unit.

22. The process of claim 13, wherein the heavy fraction in (g) is hydrotreated and then isomerized in the dewaxing unit.

23. The process of claim 13, wherein the volume flow of the naphtha/diesel fraction to the crude unit in the refinery comprises up to about 50 volume % of the total hydrocarbon flow to the crude unit.

24. The process of claim 23, wherein the naphtha/diesel flow comprises up to 20 volume %.

25. A process for converting waste plastic into chemicals useful in preparing polyethylene and lubricating oil comprising:
   (a) selecting waste plastics containing polyethylene and/or polypropylene;
   (b) pyrolyzing the waste plastics and recovering a naphtha/diesel fraction and a heavy fraction;
   (c) passing the naphtha/diesel fraction to a crude unit in a refinery; and
   (d) passing the heavy fraction to an isomerization dewaxing unit.

* * * * *